US006635163B1

United States Patent
Han et al.

(10) Patent No.: US 6,635,163 B1
(45) Date of Patent: Oct. 21, 2003

(54) ENTROPIC TRAPPING AND SIEVING OF MOLECULES

(75) Inventors: Jongyoon Han, Ithaca, NY (US); Harold G. Craighead, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/577,962

(22) Filed: May 25, 2000

Related U.S. Application Data

(60) Provisional application No. 60/137,146, filed on Jun. 1, 1999.

(51) Int. Cl.[7] .................. B01D 57/02; B01D 59/42; B01D 59/50; B01D 61/42; B01D 61/58; C02F 1/469; C08F 2/58; C07K 1/26
(52) U.S. Cl. ........................................ 204/450
(58) Field of Search ................................ 204/450

(56) References Cited

U.S. PATENT DOCUMENTS

| | | | | |
|---|---|---|---|---|
| 5,304,487 A | * | 4/1994 | Wilding et al. | 210/500.26 |
| 5,427,663 A | | 6/1995 | Austin et al. | 204/180.1 |
| 5,599,432 A | | 2/1997 | Manz et al. | 204/451 |
| 5,651,900 A | | 7/1997 | Keller et al. | 216/56 |
| 5,707,799 A | | 1/1998 | Hansmann et al. | 435/6 |
| 5,800,690 A | | 9/1998 | Chow et al. | 204/451 |
| 5,837,115 A | | 11/1998 | Austin et al. | 204/450 |
| 5,842,787 A | | 12/1998 | Kopf-Sill et al. | 366/340 |
| 5,882,465 A | | 3/1999 | McReynolds | 156/285 |
| 5,904,824 A | | 5/1999 | Oh | 204/601 |
| 5,938,923 A | | 8/1999 | Tu et al. | 210/490 |
| 5,948,227 A | | 9/1999 | Dubrow | 204/455 |
| 5,958,694 A | | 9/1999 | Nikiforov | 435/6 |
| 6,042,710 A | | 3/2000 | Dubrow | 204/454 |
| 6,043,080 A | | 3/2000 | Lipshutz et al. | 435/287.2 |
| 6,110,339 A | | 8/2000 | Yager et al. | 204/451 |
| 6,156,273 A | | 12/2000 | Regnier et al. | 422/70 |
| 6,186,660 B1 | | 2/2001 | Kopf-Sill et al. | 366/340 |
| 6,193,866 B1 | | 2/2001 | Bader et al. | 204/450 |

FOREIGN PATENT DOCUMENTS

WO    WO 98054568 A1 * 12/1998 .......... G01N/30/60

OTHER PUBLICATIONS

Chou, C., et al., "Sorting by Diffusion: An Asymmetric Obstacle Course for Continous Molecular Separation", *PNAS 96* (*24*), pp. 13762–13765, (Nov. 23, 1999).

Nixon, G. I., et al., "Entropic Trapping and electrophoretic drift of a polyelectrolyte down a channel with a periodically oscillating width", *Physical Review E, 53* (*5*), pp. 4969–4980, (May 1996).

Volkmuth, W.D., et al., "DNA electrophoresis in microlithographic arrays", *Nature, 358*, pp. 600–602 (Aug. 13, 1992).

Volkmuth, W.D., et al., "Trapping of branched DNA in microfabricated structures", *PNAS, 92* (*15*), pp. 6887–6891, (Jul. 1995).

* cited by examiner

*Primary Examiner*—Jill Warden
*Assistant Examiner*—Jennine M. Brown
(74) *Attorney, Agent, or Firm*—Schwegman, Lundberg, Woessner & Kluth, P.A.

(57) ABSTRACT

Nanofluidic entropic traps, comprising alternating thin and thick regions, sieve small molecules such as DNA or protein polymers and other molecules. The thick region is comparable or substantially larger than the molecule to be separated, while the thin region is substantially smaller than the size of the molecules to be separated. Due to the molecular size dependence of the entropic trapping effect, separation of molecules may be achieved. In addition, entropic traps are used to collect, trap and control many molecules in the nanofluidic channel. A fabrication method is disclosed to provide an efficient way to make nanofluidic constrictions in any fluidic devices.

22 Claims, 5 Drawing Sheets

ENTROPIC TRAPPING AND SIEVING OF MOLECULES

This application claims the benefit of U.S. Provisional Application No. 60/137,146, filed Jun. 1, 1999, the disclosure of which is hereby incorporated herein by reference.

This invention was made with Government support under Grant no. HG01506, awarded by NIH. The Government has certain rights in the invention.

BACKGROUND OF THE INVENTION

The present invention relates, in general, to the efficient separation of molecules such as DNA and proteins, and more particularly to a separation device including nanofluidic channels of different sizes for providing alternate thin and thick regions along a channel to act as a filtering or sieving structure.

The separation of molecules according to their sizes is an essential step in biology and other fields and in analytical procedures such as chromatography, DNA sequencing or genome mapping. Conventional methods for separating molecules include electrophoresis and chromatography, which utilize the different transport properties (mobility) of different molecules in a solution-filled capillary or column. In many cases, additional sieving material, such as a gel matrix, is required to obtain sufficient separation of the molecules to permit analysis. In a conventional gel electrophoresis, as an example, molecules such as DNA molecules are separated during an electric-field-driven motion in a highly restrictive gel matrix, because the mobility of the molecules is dependent on their length. However, this length-dependence of molecule mobility vanishes for DNA molecules longer than about 40,000 base pairs, mainly because the molecules tend to be more stretched and oriented in the direction of the applied electric field. Molecules as long as 10,000,000 base pairs can be separated by pulsing the electric field (pulsed field gel electrophoresis), but this process is usually very time consuming and inefficient.

To obtain better efficiency and control for separation process, the use of an artificial system using a precisely defined microchannel structure as a molecular sieve has been suggested. However, initial attempts to produce efficient artificial gel systems were hindered by poor understanding of the molecular dynamics in the microchannels. It has been found that the conformation (shape) of DNA or other polymer molecules has a direct impact on their motion in a restrictive medium because the interaction cross section of the molecules with obstacles is changed with conformational change. In free solution, polymer molecules such as DNA have a spherical shape in their equilibrium state, and the size of this equilibrium shape is characterized by a radius of gyration ($R_o$) of the molecule. In the separation process of DNA or other polymers, it is important to maintain the conformation of the molecule in its equilibrium shape as much as possible, because otherwise the polymeric molecule will stretch out in the direction of the motion, rendering the mobility of the molecule length (size) independent. This is because there is minimal difference in their interaction with a retarding matrix such as gel or obstacles.

In terms of the fabrication of artificial gel systems, current photolithography techniques are limited in resolution at about the 1 micrometer level. Therefore, one cannot easily make constrictions or obstacles small enough for the separation of important molecules (DNA, proteins etc). Electron beam lithography can fabricate smaller features but it generally is too expensive, and it is difficult to produce a large-area device with this process.

It became clear that a more careful design of a separation device, combined with an inexpensive technique that can produce many ultrasmall constrictions over a large area, is essential in developing a functioning molecular separation device.

SUMMARY OF THE INVENTION

When molecules become relaxed or are in their equilibrium spherical shape, their interaction with a retarding matrix can be dependent on the molecule's radius of gyration ($R_o$), and in turn on the length of the molecule. Accordingly, a design for a molecule sieving structure should include a somewhat open area where molecules can relax, as well as narrow constrictions that can serve as a molecular sieve.

It is, therefore, an object of the present invention to provide a separation device incorporating nanofluidic constrictions (thin regions) and obstacle free regions (thick regions), through which molecules can be caused to flow either by electrophoresis or by non-electric forces.

Briefly, the device of the invention provides a flow channel incorporating alternating thin and thick regions which operate as a filter, or sieving structure. The thin regions are sufficiently small to act as constrictions to the flow of small objects, such as DNA molecules, proteins, cells, viruses, or other similarly-sized particles, while the thick regions allow molecules to relax for more efficient separation at the thin region. To this end, the thick region depth may be made comparable to, or substantially larger than, the size of a molecule (for example, the radius of gyration $R_o$ for polymer molecules) to be sieved. Also the thin region depth may be made substantially smaller than the size of the molecule or other object to be sieved. Although the device of the invention can be used to filter a variety of objects, the following description will be in terms of molecules, and particularly DNA molecules for convenience.

Accordingly, the present invention is directed to a nanofluidic channel in which the motion of molecules such as DNA molecules is characterized by the provision of molecular traps. In accordance with the invention, an elongated nanofluidic channel is provided with alternating regions of thick and thin gaps along its length. The equilibrium spherical shape of a molecule such as DNA or protein has a radius of gyration $R_o$, which is the shape the molecule assumes when it is relaxed in an open region, such as in the thick regions of the channel. If the molecule is forced to enter a constriction that is much less than $R_o$, the molecule has to be deformed from its equilibrium shape. Since such a deformation is entropically unfavorable, a driving force is required to force the molecule to enter the constriction. This effect is referred to as the entropic trapping of a long polymer, and this effect is crucial in the operation of present invention.

The entropic trapping effect can be utilized in operations such as molecular trapping, molecular band formation, molecular separation and sieving, and molecular flow manipulation in nanofluidic or microfluidic channels. The separation or sieving can be achieved when a suitable driving force is supplied to trapped molecules, when they migrate across many molecular traps and get separated because of the size-dependent trapping effect. Just before the migration through the thin regions, molecules are sieved by entropic trapping effect. After the molecules pass through the thin region, they relax back to their equilibrium shape quickly because of the existence of the thick regions. This process is repeated many times until the required separation is achieved. By controlling the driving force for the molecules, molecular trapping and manipulation can be achieved with the same structure.

In accordance with one embodiment of the invention, a new method was used to fabricate a nanofluidic channel having narrow constrictions (thin regions), spaced along the length of the channel, with the depth of the thin regions ranging between about 10 nm and about 500 nm, and having relatively thick regions between adjacent constrictions, of between about 0.5 micrometer and about 10 micrometer. Channels of these approximate dimensions may be referred to herein as nanofluidic channels, or simply as nanochannels. In accordance with this method, channels with variable depths were defined and etched in a silicon substrate, or wafer, using two-level photolithography. After a thermal oxidation process, mainly for electrical isolation, the top surface of the device was covered with a thin transparent plate. This technique permitted easy fabrication of very narrow gaps or constrictions without the need for e-beam lithography for the patterning of sub-micrometer features. This process was accomplished by the use of differential etching of two regions and the bonding of a capping layer.

BRIEF DESCRIPTION OF DRAWINGS

The foregoing and additional objects, features and advantages of the present invention will be apparent to those of skill in the art from the following detailed description of preferred embodiments thereof, taken in conjunction with the accompanying drawings, in which.

DESCRIPTION OF PREFERRED EMBODIMENT

Figure 1:
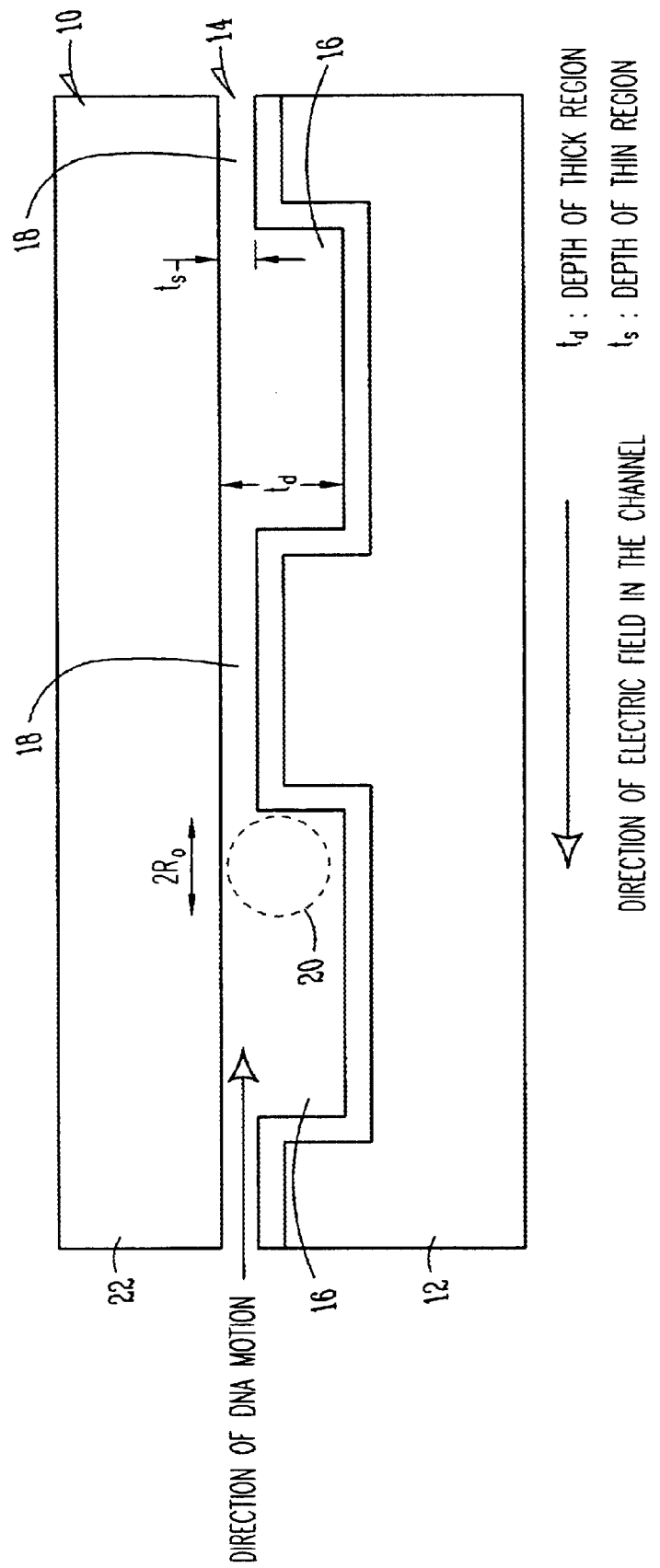
FIG. 1 is a diagrammatic cross sectional view of an entropic trapping nanochannel in accordance with the present invention.

Turning now to a more detailed consideration of the present invention, there is illustrated in FIG. 1 a nanofluidic sieving device 10 in accordance with the present invention. The device 10 includes a silicon wafer or substrate 12 in which is fabricated a nanofluidic channel 14 having alternating thick regions 16 and thin regions 18 along its length. The channel 14 preferably is covered by a transparent top plate 22 which is bonded to the substrate 12 along the edges of the channel. The nanochannel 14 is filled with a buffer solution or other liquid containing DNA molecules or other polymer molecules 20 to be separated. It will be understood that any desired material such as glass or plastic may be used as the substrate 12, and as the transparent coverplate 22, and any conventional bonding techniques can be used to seal the coverplate 22 to a particular substrate 12.

In the illustrated embodiment of the invention, which is specific for DNA molecule separation by way of example, the thick regions 16 may be between about 0.5 micrometers and 5 micrometers in depth, or thickness, while the thin regions may be between 50 and 200 nm in depth, or thickness. The thicknesses of the thick and thin regions can be varied according to the size of the molecule 20 to be separated. The thin region 18 thickness (defined as $t_s$) is substantially smaller than the radius of gyration $R_o$ of the DNA or other polymer molecule 20 to be separated. The thick region 16 thickness (defined as $t_d$) is compatible to $R_o$ of a molecule 20 to be separated, and thus to a typical long DNA or other polymer molecule, allowing the molecule to relax to its equilibrium spherical shape in this region. Because molecules can relax in the thick regions 16, they are entropically hindered from entering the thin regions 18 of the channel. When a molecule 20 to be separated is driven through the nanochannel 14 by an electric field or by hydrodynamic pressure, the motion of the molecule 20 will be retarded whenever it reaches the thin regions 18.

Figure 2:
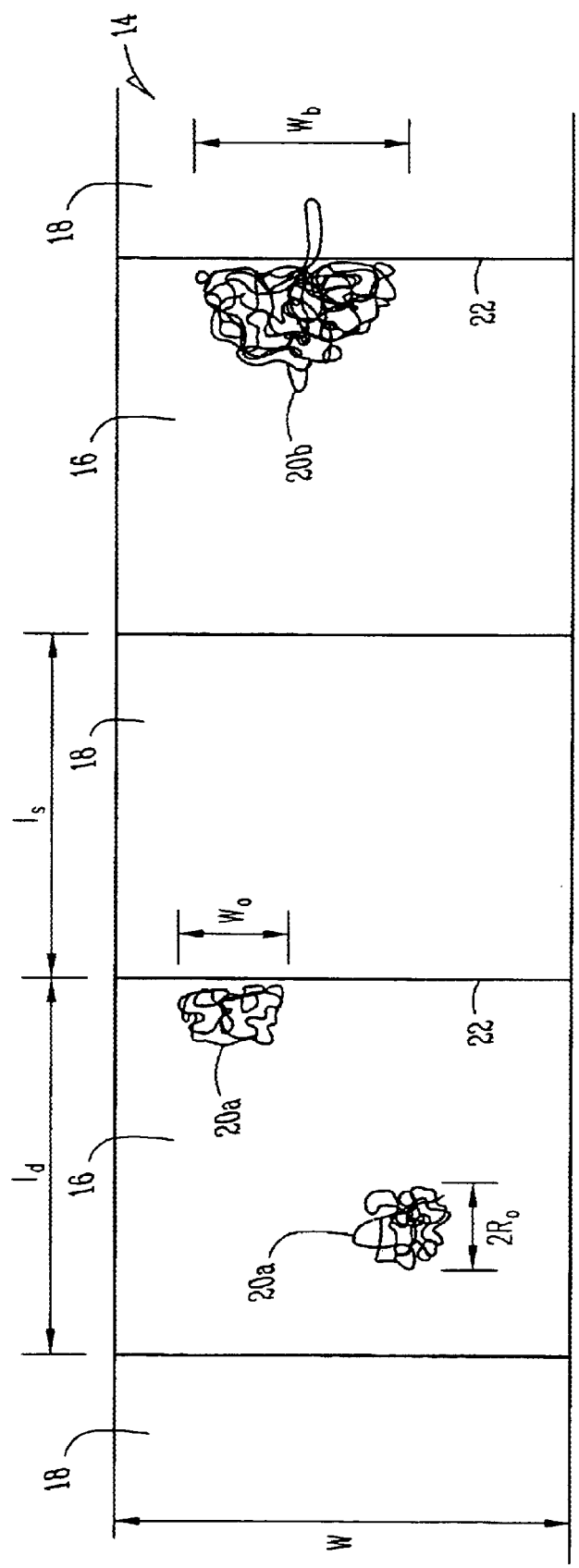
FIG. 2 is a diagrammatic top plan view of an entropic trap, which illustrates the separation mechanism.

FIG. 2 is a top view of the nanofluidic sieving channel 14 where two different DNA molecules or polymers 20a (smaller) and 20b (larger) were driven toward the right-hand end of the channel. Both molecules 20a and 20b are trapped at starting points 22 of the thin regions 18. The larger molecule 20b has a wider contact area with the thin region 18, as compared with the smaller molecule 20a ($w_a < w_b$), which makes the larger molecule 20b have a higher probability of escaping the trapping point and progressing through the 20 channel.

The length of the thin region 18 (defined as $l_s$) and the length of the thick region 16 (defined as $l_d$) along the length of elongated nanochannel 14 can be varied to accommodate molecules with different $R_o$ and length. Changing $l_d$ changes the relaxation of the molecule after it escapes the thin region 18. As the size of the molecule 20 increases, $l_d$ should be increased to accommodate the increased relaxation time required for big molecules to relax back to equilibrium shape. In the illustrated embodiments, the nanofluidic channel is 30 micrometer wide (W), although other widths can be provided. It will be understood that any desired number of nanochannels with any desired combination of values of $l_s$, $l_d$, W, $t_s$, $t_d$ may be provided on a wafer, or substrate.

Figure 3:
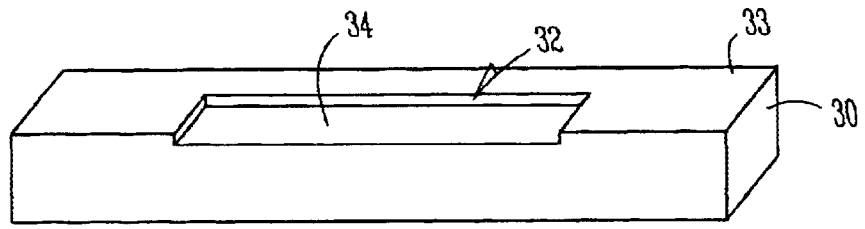
FIGS. 3 through 7 diagrammatically illustrate the fabrication process for the nanofluidic sieving device of the present invention.
Figure 4:
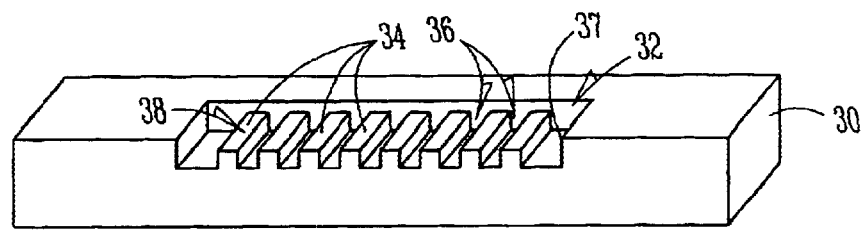
Figure 5:
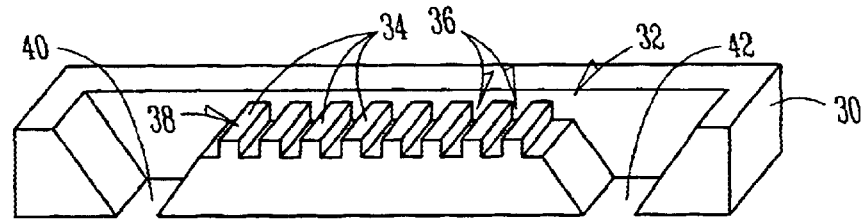

As illustrated in FIGS. 3 through 7, nanofluidic channels such as the channels 14 illustrated in FIGS. 1 and 2, may be fabricated on a silicon wafer 30 by a photolithography and reactive ion etching technique. In an experimental fabrication of nanochannels in accordance with the invention, as illustrated in FIG. 3, a channel 32 was defined on the top surface 33 of the wafer 30 by standard photolithography, and was etched by a reactive ion etch (RIE), providing a channel having a floor 34. Thereafter, as illustrated in FIG. 4, a second level of photolithography and chlorine RIE etching with an oxide mask were used to make spaced thick regions 36 within the channel 30. This etching step was performed in the floor 34 of the channel 32 (FIG. 3) to produce a second, lower floor 37 in each of the thick regions, leaving in the channel a series of parallel transverse barriers 38 spaced apart along the length of the channel 32 between the thick regions. The barriers form the ends of the thick regions of the channel (region 16 in FIG. 1) with the tops 34 of the barriers forming the thin regions. The structural parameters $l_s$, $l_d$, W, $t_s$, $t_d$ in FIG. 1 can be easily varied during these first two lithography steps with a high precision, and according to the specific needs of the device.

After completing the channel 32, a pair of loading/unloading apertures 40 and 42 were fabricated at opposite ends of the channel by potassium hydroxide (KOH) etch-through using a silicon nitride etch mask. One of the two apertures 40 and 42 may serve as an inlet for a buffer solution or other liquid, containing molecules to be separated, while the other aperture may serve as the outlet for the solution and the separated molecules. Alternatively, the aperture need not be fabricated, but the channel 32 may instead be connected to other microfluidic or nanofluidic channels or chambers that have different functions, to form an integrated system.

Figure 6:
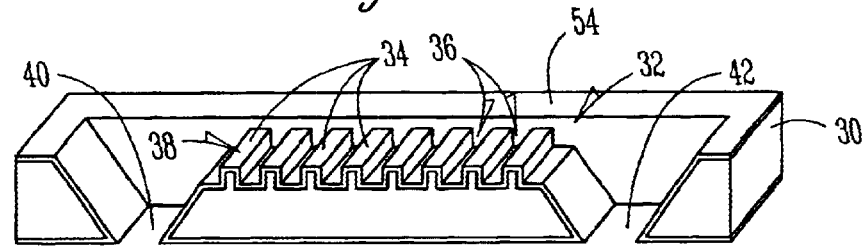

As illustrated in FIG. 6, a thermal oxide layer 50 may be grown on all of the surface of the channel 32 and on the surface of the wafer to a thickness of up to 400 nm to provide electrical isolation between the buffer solution and the silicon substrate. In the case where a non-conducting substrate, or wafer 30, such as glass is used, this step may be omitted.

Figure 7:
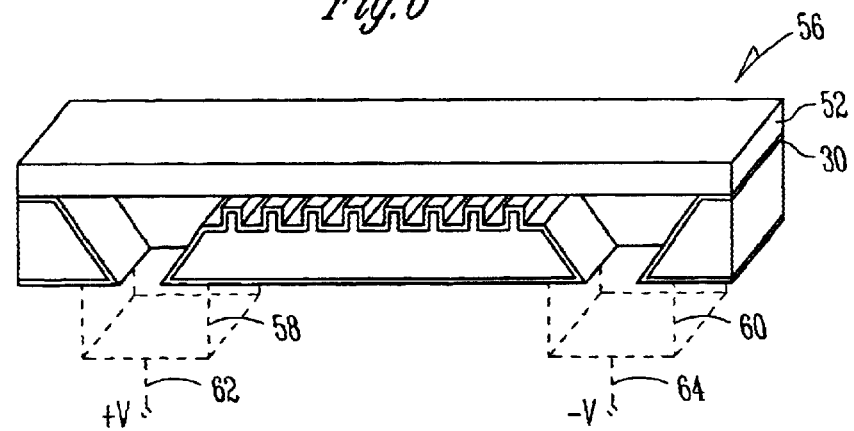

Finally, as illustrated in FIG. 7, the top of the channel 32 was hermetically sealed with a thin glass coverslip 52 secured to the top surface 54 of the silicon substrate 30 and its oxide coating 50, as by anodic bonding, to provide the nanofluidic channel 56. The coverslip 52 may be a thin Pyrex glass or other suitable material to close the channel and to provide a fluid path across the barriers 38 from the inlet end 40 to the outlet end 42. In the case of using substrates 30 other than silicon, the hermetic seal may be obtained by suitable bonding techniques such as glass-to-glass fusion bonding or bonding with an intervening thin glue layer. The coverplate 52 is thin and transparent enough to allow the detection of separated molecules.

Figure 8:
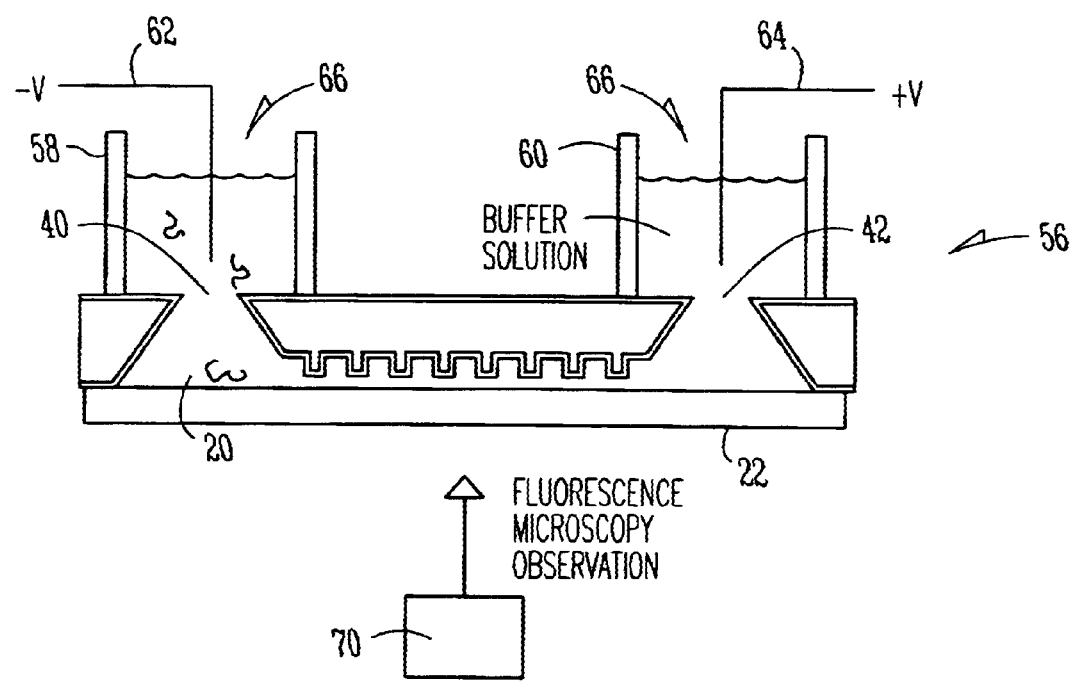
FIG. 8 illustrates one embodiment of the nanochannel of the invention in combination with cathode and anode electrodes and two loading reservoirs.

In one preferred embodiment of a nanofluidic channel device, as illustrated in FIG. 8, the nanofluidic sieving device 56 illustrated in FIG. 7 is turned upside down, and two liquid reservoirs 58 and 60, respectively, are attached. Metallic wires 62 and 64, preferably noble metals such as platinum or gold, may be inserted into the reservoirs 58 and 60 respectively, to make a cathode 66 and an anode 68. A voltage V applied across the electrodes produces separation of molecules 20, which is detected from the bottom side through the transparent coverplate 22 of the device 10. The detection of molecules 20, as an example not as a limitation, may be done by using a fluorescent dye attached uniformly to the molecules 20 and observing in the channel by an optical microscope 70 or equivalent optical detection system.

Figure 9:
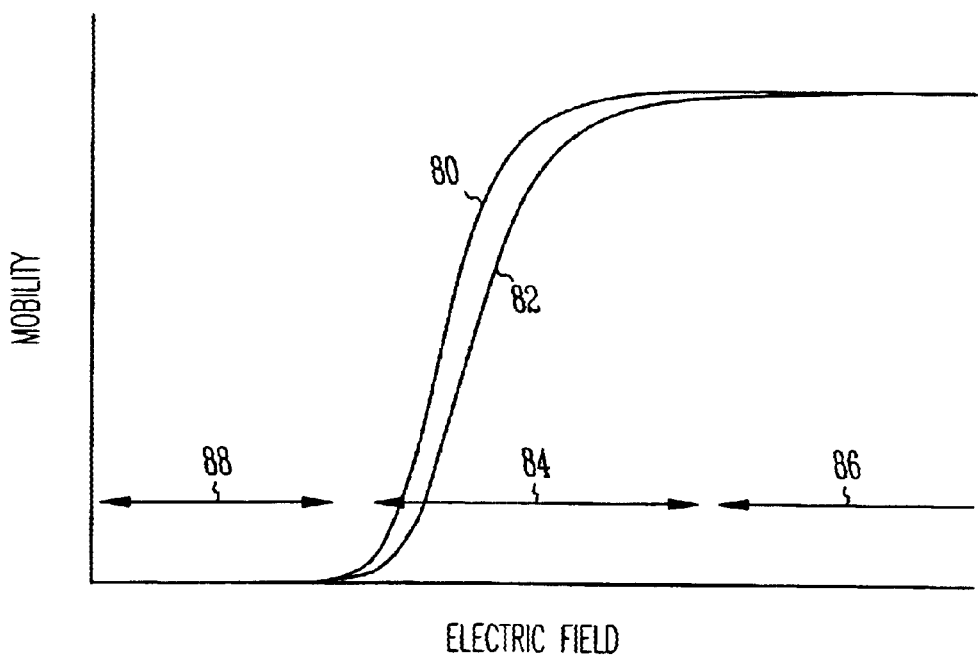
FIG. 9 graphically illustrates the mobility of two different DNA species versus electric field in a nanofluidic sieving channel.

FIG. 9 is a graphical illustration of the mobility of two different (large and small) molecules versus the electric field applied as a driving force to the nanofluidic sieving channel. The driving force for the molecules in the channel may also come from hydrodynamic pressure if desired, and in such a case the pressure will be the relevant quantity, instead of the electric field as given in this example. It is understood that the mobility curves plotted versus the electric field have a sigmoidal shape as shown in FIG. 9. The curve 80 for larger polymer molecule should be higher than the curve 82 for a smaller polymer in a particular range 84 of the electric field. If electric field is higher (in the range 86), the mobility is the same irrespective of the molecule size, because the driving force is too strong and the entropic trapping is negligible. If the electric field is lower (in the range 88), then the entropic trapping is so strong that molecules are trapped indefinitely, irrespective of their size. The electric field applied to the nanofluidic channel should be adjusted to the level corresponding to the range 84. The specific value for this range may vary for a specific molecules to be separated. If the electric field is adjusted to the range 86, all the molecules move at the same speed, irrespective of the size. Therefore, this range 86 may be used for recollection of already separated molecules or moving the mixture of DNA molecules from one location to another without fractionating them. The electric field range 88 allows molecules to be collected at the first entropic barrier, because in the range 88 the entropic trapping effect is too severe for DNA to overcome even a single entropic barrier within a reasonable amount of time.

Figure 10:
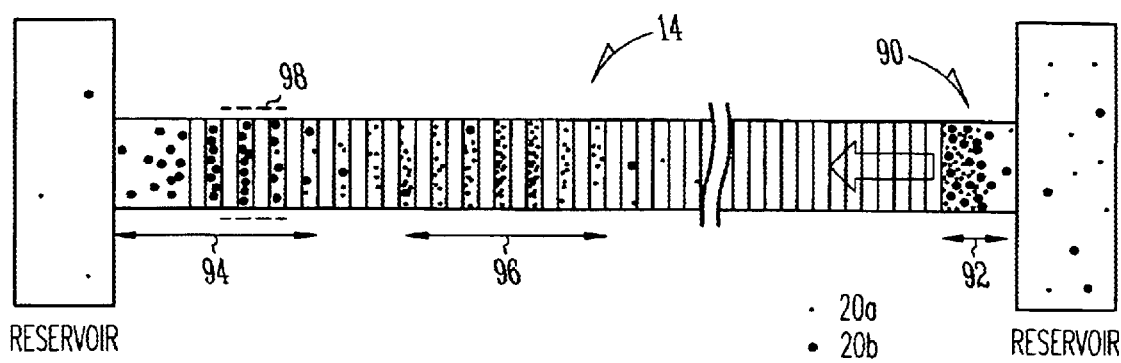
FIG. 10 illustrates the collection of DNA, launching, separation and detection of DNA bands, in one preferred embodiment of the invention.

As illustrated in FIG. 10, by way of an example and not limitation, if a number of molecules are supplied to channel 14, as by way of reservoir 60 and aperture 42, and an electric field in the range 88 in FIG. 9 is applied for a specific amount of time along the nanofluidic sieving channel 14, one can collect many DNA or polymer molecules 20 at the first entropic trap 90, yielding a highly defined and concentrated molecule band 92. The concentrated band 92 may be launched into the nanochannel for band separation by switching the electric field from the value in the range 88 of FIG. 9 to the value in the range 84 of FIG. 9. In this illustrated embodiment of the invention, two different types of DNA (20a and 20b, small and large DNA, respectively) are mixed in the band 92. When launched into the nanochannel, the band 92 becomes separated, as it migrates through many entropic traps along the channel, into two bands, a first band 94 and a second band 96. It is understood that the first band is composed of larger DNA 20b, while the second band is composed of smaller DNA 20a.

For the detection of this separation, in one preferred embodiment, one may set up a region of interest 98 and collect the fluorescent signal from the bands 94 and 96, either optically or using other suitable methods, as a function of time. The separated bands 94 and 96, may then be recollected at the other end of the channel sequentially, preferably in aperture 40 and reservoir 58, or other fluidics channels may be used to redirect each band into separate microfluidic chambers.

It is imperative to note that the above-mentioned method may be utilized to fractionate mixtures with any number of different types of molecules, as the resolution permits. The resolution may be improved by applying several different optimization techniques. Having a longer channel is one way, but another important method is changing the various structural parameters mentioned in, FIG. 1 to get optimized results. For certain polymer molecules, one may optimize a specific set of conditions, including but not limited to, the structural parameters illustrated in FIG. 1, the electric field or the electric field range 84 of FIG. 10, and the overall length of the nanochannel.

Figure 11:
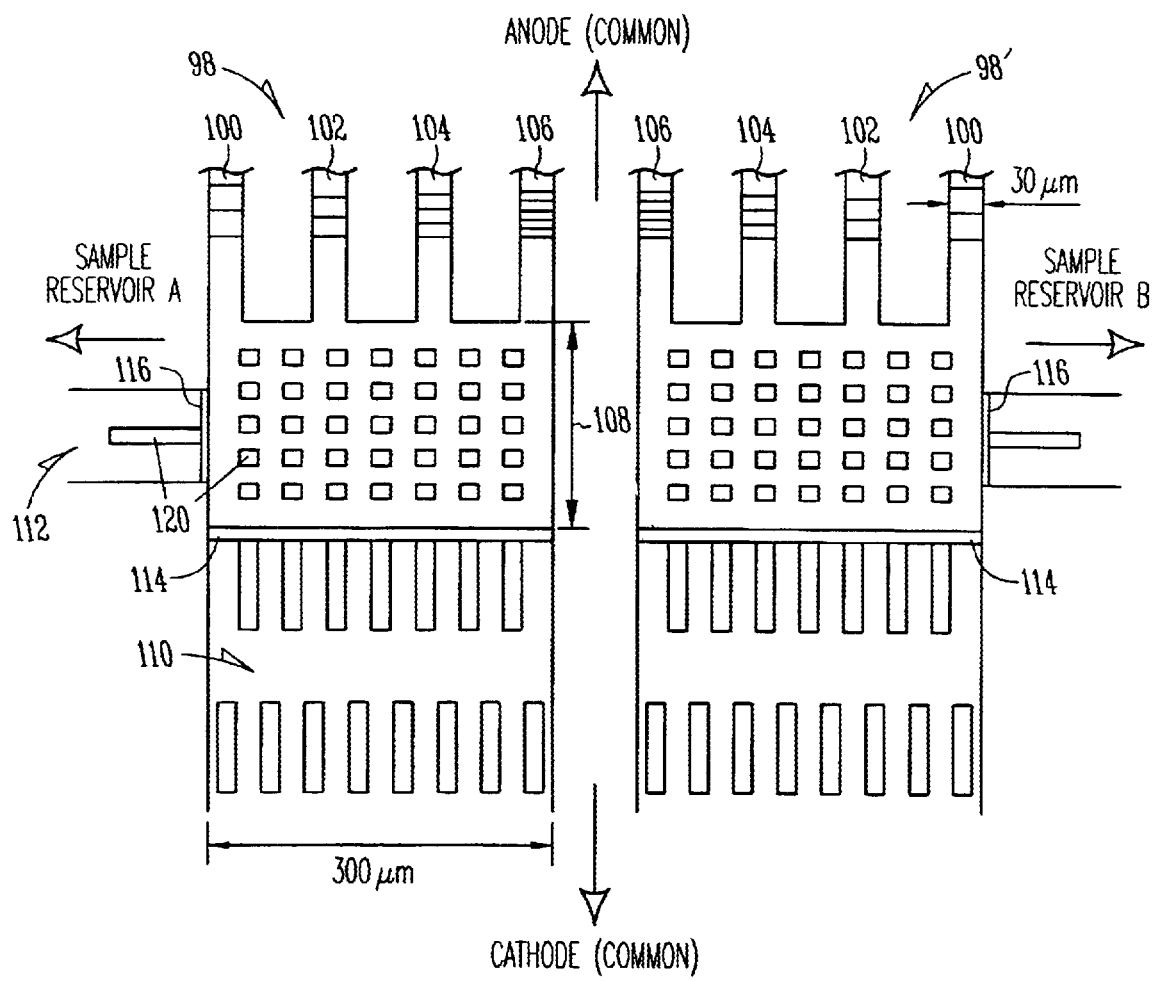
FIG. 11 is a diagrammatic top plan view of a multiple channel entropic trap device, where two different DNA samples can be loaded and separated simultaneously.

As diagrammatically illustrated in the top plan view of FIG. 11, by way of example and not limitation, a multiple channel device 98, which is capable of separating multiple samples simultaneously, may be fabricated. In this embodiment of the invention, several nanofluidic sieving channels 100, 102, 104 and 106, each with a different sieving structural parameter, are connected to a larger loading and collection chamber 108. The different structural parameters are optimized for the separation of different length ranges of molecules to be separated. The number of nanochannels which may be connected to a loading or collection chamber 108 may be increased without any difficulty in the fabrication or operation of the device, mainly to accommodate wide variety of molecules. The loading and collection chamber 108 is connected to the cathode by a wider channel 110, and to a reservoir of sample solution by a loading channel 112. In addition, the central collection chamber 108 is defined by two entropic barriers 114 and 116, which enable manipulation of the molecules to be separated, which are in the central collection chamber 108. The central chamber 108, the loading channel 112 and the channel 110 are all supported by a supporting pillar structure 120, mainly to prevent possible collapse of the coverplate (roof) of the channel down to the bottom.

In the embodiment of the invention illustrated in FIG. 11, there are two multiple channel devices 98 and 98's, having two separate loading and collection chambers 108 connected to two separate sample reservoirs (sample reservoirs A and B). Each loading and collection chamber 108 is connected to the same sets of nanofluidic sieving channels 100, 102, 104 and 106, with various structural parameters, and eventually all of these nanochannels 100 lead to a common anode, whereas the two loading chambers 108 also lead to a common cathode.

In the operation of the device of FIG. 11, two different samples of molecules, possibly one unknown sample to be analyzed and one known control or reference sample with size information about the fragments in the sample (in DNA analysis for example, a DNA ladder sample could serve as a reference) may be introduced into sample reservoirs. For loading the molecules into the channels, a suitable electrical potential may be applied between the cathode and the sample reservoirs, causing the molecules to enter the loading channel 112, the central collection chamber 108, and the channel to the cathode 110. As a result, the central chamber 108 would be evenly filled with molecules to be separated. Then another electric field is applied between the cathode and the anode, causing molecule transport to the nanofluidic sieving channels 100, 102, 104 and 106. The electric field between the cathode and the anode may be selected to have a value in the electric field range 88 of FIG. 9, so the molecules are collected at the very first barriers of each nanochannel. With this low electric field, the molecules behind the entropic barrier 114 cannot drift into the central collection chamber 108, but pile up behind the barrier 114. Additionally the existence of the barrier 116 makes sure that the molecules in the loading channel 112 do not drift into the central chamber 108 since there is no substantial electric field existing between the sample reservoir and the cathode. Therefore, only the molecules in the collection chamber 108 can drift into the nanochannels, providing the concentrated band discussed with respect to FIG. 10 which will be launched into each of the nanochannels.

After this process, the field may again be developed between the cathode and the sample reservoirs, causing the remainder of the molecules behind the entropic barrier 114 to be drained back to the sample reservoir, without affecting the collected molecules at the first barriers of the nanochannels 100, 102, 104 and 106. This process permits control of the concentration of molecules in the launching band, which is relevant in the separation process. Also, the same process can be repeated as many times as desired, to obtain even higher concentrations of the molecules in the band.

As the separation process proceeds, the data taken from different samples can be easily detected and compared, enabling more reliable analysis. It is important to know that the number of samples to be analyzed may be increased as desired without any serious technical and operational difficulties.

Thus, there has been disclosed a nanofluidic channel for use in entropic trapping and sieving of polymer molecules such as DNA and proteins. The channel includes alternating thick and thin segments, or sections, which alternately cause DNA or other polymer molecules to stretch and to return to a rest equilibrium configuration. The channel permits separation of long polymers in a DC applied electric field, with the device structure affecting the mobility of the molecules as they pass through the channels. Entropic traps have other uses in manipulating and collecting many molecules, with a high degree of control, into a narrow band, which is useful in the separation process. Although the invention has been disclosed in terms of preferred embodiments, it will be apparent that variations and modifications may be made without departing from the true spirit and scope thereof as set forth in the following claims.

What is claimed is:

1. A nanofluidic device comprising:
   at least one channel including a combination of constrained and unconstrained regions, so that the constrained regions in the channel delay passage of objects, and the unconstrained regions in the channel having a thickness greater than that of said constrained regions, and being large enough to allow the passage of said objects, wherein the delay for larger objects is less than the delay for smaller objects.

2. The device of claim 1, further including channels leading from said at least one channel to fluidic components.

3. The device of claim 2, further including a force to drive said objects through said channel.

4. The device of claim 3, further including inlet and outlet apertures for said channel.

5. The device of claim 4, wherein a part of said combination of constrained and unconstrained regions is used to collect and trap said objects.

6. The device of claim 5, wherein said constrained regions are used to control the flow of said objects in microfluidic channels and chambers.

7. The device of claim 6, wherein at least some of said constrained and unconstrained regions contains supporting structures to maintain the uniformity of the thickness of the said regions.

8. The device of claim 7, wherein said constrained and unconstrained regions are alternately spaced along said channel.

9. The device of claim 8, wherein the depth of said constrained region is between about 5 nm and about 500 nm.

10. The device of claim 9, wherein the depth of said unconstrained region is between about 0.1 micron and about 10 micron.

11. The device of claim 10, further including means for applying a voltage across said channel for producing electrophoresis of said objects.

12. The device of claim 11, further including fluidic channels for introducing said objects into the channel.

13. The device of claim 12, further including multiple nanofluidic sieving channels, optimized for different size range, for receiving a mixture of wide variety of objects.

14. The device of claim 13, further including a fluidic chamber, bounded by said regions for collecting molecules into a narrow band for further analysis.

15. The device of claim 14, further including multiple loading and collection chambers, which are separate from one another, each containing a set of multiple channels for the analysis of multiple samples.

16. The nanofluidic device of claim 1 wherein the delay is inversely related to he size of the object.

17. A method for separating DNA molecules, proteins, cells or other similar-sized objects, comprising:
   supplying molecules in a fluid to a nanofluidic channel having alternating constrained and unconstrained regions, the constrained regions being smaller than the size of the molecule to be separated, and the unconstrained region being substantially close to or larger than the size of the molecule to be separated; and, applying a driving force to cause said molecules to move along said channel through said regions, the constrained regions causing delay of passage of selected molecules, wherein the delay for larger molecules is less than the delay for smaller molecules.

18. The method of claim 17, further including, prior to supplying the molecules, selecting a channel having a channel length of the unconstrained regions based on the relaxation property of the molecules to be separated.

19. The method of claim 17, further including collecting many molecules into a narrow band, by way of applying an appropriate driving force and constrained regions in the microfluidic or nanofluidic channels.

20. The method of claim 19, further including launching the collected molecules by suddenly increasing the applied driving force, enabling molecules to escape the constrained regions.

21. The method of claim 20, where the delay induced by the constrained regions is due to an entropic barrier.

22. The method of claim 20 wherein the delay is inversely related to the size of the molecule.

* * * * *